(12) United States Patent
Kato

(10) Patent No.: US 7,755,750 B2
(45) Date of Patent: Jul. 13, 2010

(54) METHOD OF DETECTING POROUS MATERIAL DEFECT

(75) Inventor: Shigeki Kato, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 12/235,204

(22) Filed: Sep. 22, 2008

(65) Prior Publication Data

US 2009/0051909 A1 Feb. 26, 2009

Related U.S. Application Data

(63) Continuation of application No. PCT/JP2006/325939, filed on Dec. 26, 2006.

(30) Foreign Application Priority Data

Mar. 28, 2006 (JP) .............................. 2006-087258

(51) Int. Cl.
*G01N 21/00* (2006.01)

(52) U.S. Cl. ................. 356/237.1; 356/237.6

(58) Field of Classification Search ... 356/237.1–237.6, 356/335–343; 250/574

See application file for complete search history.

(56) References Cited

U.S. PATENT DOCUMENTS

| | | | |
|---|---|---|---|
| 5,411,682 A | 5/1995 | Nagashima | |
| 5,640,236 A | 6/1997 | Nagashima | |
| 7,012,678 B2 * | 3/2006 | Enomoto et al. | 356/237.1 |
| 2003/0048941 A1 * | 3/2003 | Minami | 382/165 |
| 2003/0112437 A1 | 6/2003 | Enomoto et al. | |
| 2003/0174320 A1 * | 9/2003 | Yokoyama et al. | 356/237.6 |
| 2006/0133563 A1 * | 6/2006 | Hopkins et al. | 378/5 |
| 2006/0151926 A1 * | 7/2006 | Zoeller, III | 264/603 |
| 2006/0174695 A1 | 8/2006 | Miyashita et al. | |
| 2007/0022724 A1 * | 2/2007 | Gargano et al. | 55/523 |

(Continued)

FOREIGN PATENT DOCUMENTS

JP A 06-134268 5/1994

(Continued)

*Primary Examiner*—Hoa Q Pham
(74) *Attorney, Agent, or Firm*—Oliff & Berridge, PLC

(57) ABSTRACT

A method of detecting a defect in a porous body (1) includes applying a light beam (13) to fine particles (12) discharged from the porous body (1), and detecting the light and shade of scattered light caused by the fine particles (12) to detect the position of a defect, wherein the light and shade of the scattered light is detected at a position facing the light beam (13). When a light source that emits the light beam (13) is defined as an origin (11), a position in a plane formed by the light beam (13) corresponding to a center of an end face of the porous body (1) through which the fine particles (12) are discharged is defined as a center point (C2), a straight line that extends from the origin (11) toward the center point (C2) is defined as $l_1$, a straight line that extends from the origin (11) toward a detection position (16) of the scattered light is defined as $l_2$, and the angle formed by the straight line $l_1$ and the straight line $l_2$ in the plane formed by the light beam (13) is defined as $\theta_1$, the light and shade of the scattered light is preferably detected at a detection position (16) at which the angle $\theta_1$ is 0 to 80°. According to this method, a defect can be detected with high sensitivity.

5 Claims, 4 Drawing Sheets

U.S. PATENT DOCUMENTS

| | | | |
|---|---|---|---|
| 2007/0132988 A1 * | 6/2007 | Gargano et al. | 356/237.6 |
| 2008/0173071 A1 * | 7/2008 | Park et al. | 73/38 |

FOREIGN PATENT DOCUMENTS

| | | | |
|---|---|---|---|
| JP | A 2000-065673 | 3/2000 | |
| JP | A 2000-193582 | 7/2000 | |
| JP | A 2002-357562 | 12/2002 | |
| JP | A 2004-286703 | 10/2004 | |

* cited by examiner

FIG.5
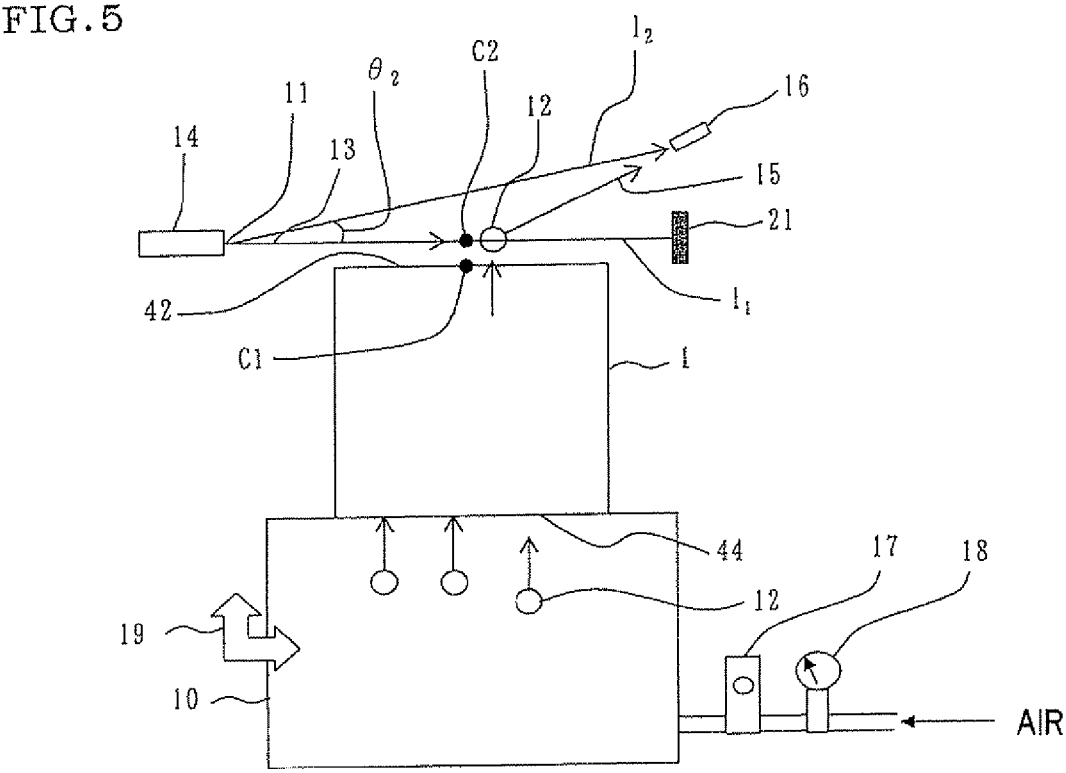
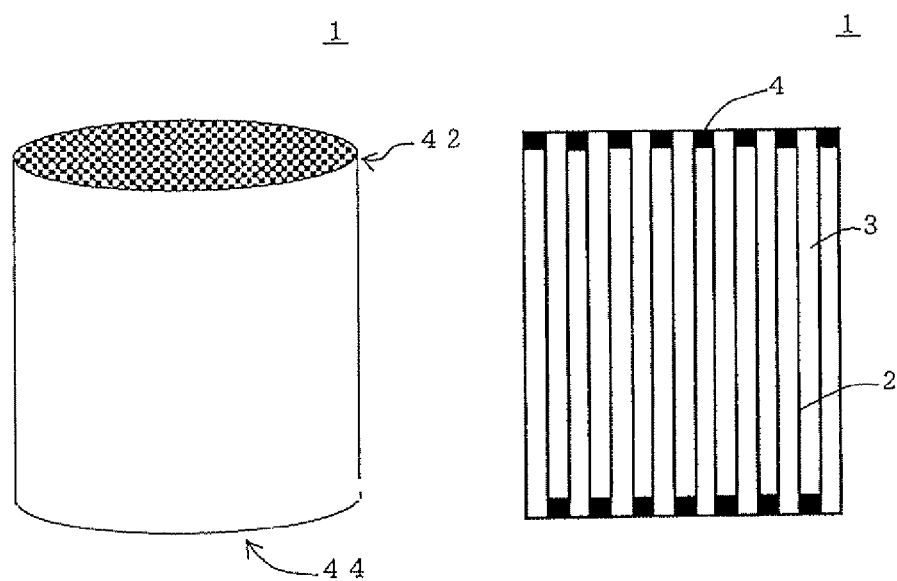
FIG.6(a)  FIG.6(b)

METHOD OF DETECTING POROUS MATERIAL DEFECT

TECHNICAL FIELD

The present invention relates to a method of detecting a defect in a porous body used for filters and the like. More particularly, the present invention relates to a method that can detect a defect in a porous body with high sensitivity.

BACKGROUND ART

A porous body has been widely used for filters and the like. For example, a porous body has been used for liquid (e.g., service water or sewage) filtration devices and the like. A porous body has also been used to trap and remove fine particles contained in a dust-containing gas (e.g., exhaust gas discharged from a diesel engine).

As a method of detecting a defect in a porous body used for such purposes, a method that applies laser light to fine particles discharged from a defect in a hollow fiber membrane or a honeycomb structure, and detects the laser light scattered by the fine particles to specify the fine particle discharge position, has been proposed (see Patent Documents 1 to 3, for example).

The above-mentioned method can determine the presence or absence of a defect in a porous body and specify the position of a defect in a short period of time. Moreover, a post-treatment is easy or unnecessary. Therefore the above-mentioned method is very useful.

Patent Document 1: JP-A-6-134268
Patent Document 2: JP-A-2002-357562
Patent Document 3: JP-A-2004-286703

DISCLOSURE OF THE INVENTION

An object of the present invention is to improve the above-mentioned method, and provide a method of detecting a defect in a porous body with improved detection sensitivity.

The inventor of the present invention conducted studies in order to achieve the above object. As a result, the inventor found that the light and shade of scattered light can be detected with high sensitivity at a detection position differing from a detection position employed in a related-art method. Specifically, a related-art method detects fine particles by observing scattered light in a direction perpendicular to the laser light or a direction on the side of the light source that emits the laser light. The inventor found that the detection sensitivity is improved by observing the light and shade of scattered light at a position facing the laser light. The present invention was conceived based on the above finding, and provides the following method of detecting a defect in a porous body.

[1] A method of detecting a defect in a porous body, the method comprising applying a planar light beam to fine particles discharged from the porous body, and detecting the light and shade of scattered light caused by the fine particles to specify the position of a defect, the light and shade of the scattered light being detected at a position facing the light beam.

[2] The method according to [1], wherein, when a light source that emits the light beam is defined as an origin, a position in a plane formed by the light beam corresponding to a center of an end face of the porous body through which the fine particles are discharged is defined as a center point, a straight line that extends from the origin toward the center point is defined as $l_1$, a straight line that extends from the origin toward the detection position of the scattered light is defined as $l_2$, and the angle formed by the straight line $l_1$ and the straight line $l_2$ in the plane formed by the light beam is defined as $\theta_1$, the light and shade of the scattered light is detected at a detection position at which the angle $\theta_1$ is 0 to 80°.

[3] The method according to [1] or [2], wherein, when a light source that emits the light beam is defined as an origin, a straight line that extends from the origin toward the detection position of the scattered light is defined as $l_2$, and the angle formed by the plane formed by the light beam and the straight line $l_2$ is defined as $\theta_2$, the light and shade of the scattered light is detected at a detection position at which the angle $\theta_2$ is 10 to 80°.

[4] The method according to any one of [1] to [3], wherein the distance between the origin and a fine particle discharge end face of the porous body is 1 to 10 mm.

[5] The method according to any one of [1] to [4], wherein the porous body is a filter.

[6] The method according to any one of [1] to [5], wherein the filter is a diesel particulate filter.

Since the method according to the present invention detects the light and shade of scattered light at a specific position, a defect can be detected with high detection sensitivity.

BRIEF DESCRIPTION OF TIE DRAWINGS

FIG. 5 is a schematic side view showing a further example of a detection device used for a detection method according to the present invention.

FIG. 6(a) is a schematic oblique view showing an example of a honeycomb structure used for a diesel particulate filter, and FIG. 6(b) is a schematic cross-sectional view of the honeycomb structure.

EXPLANATION OF SYMBOLS

Figure 1:
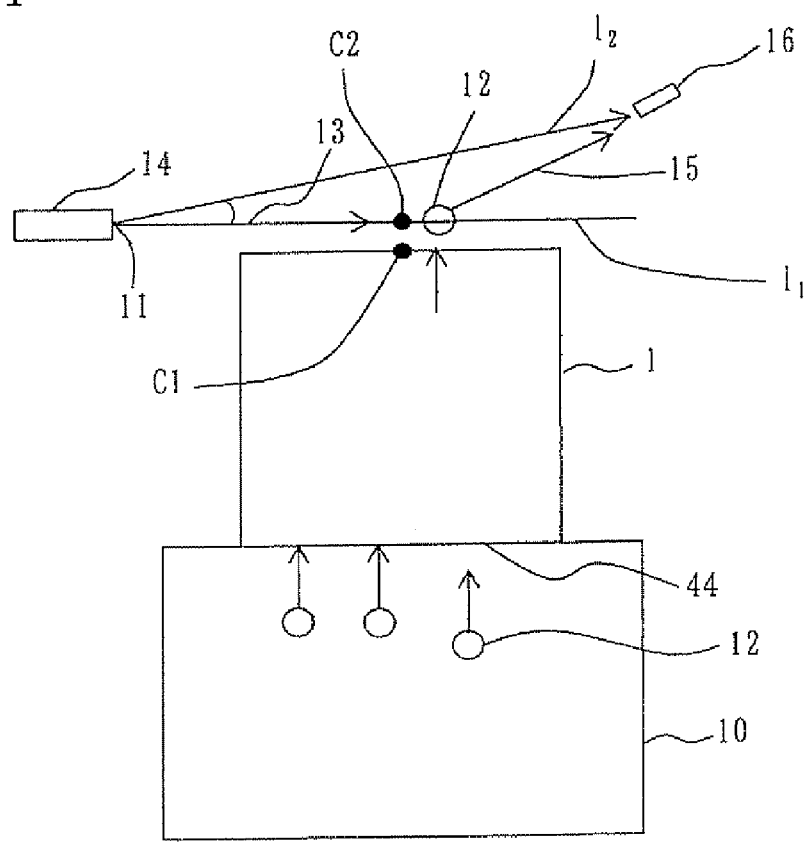
FIG. 1 is a schematic side view showing an example of a detection device used for a detection method according to the present invention.

1: honeycomb structure (porous body), 2: partition wall, 3: cell, 4: plugging portion, 10: fine particle chamber, 11: origin, 12: fine particle, 13: light beam, 14: light source, 15: scattered light, 16: detection position, 17: flowmeter, 18: pressure gage, 19: differential pressure gauge, $l_1$: straight line that extends from origin toward center point, $l_2$: straight line that extends from origin toward detection position, 20: plane formed by light beam, 21: shading plate, 42: the other end face (end face where fine particles are discharged), 44: one end face, C1: center, C2: center point

BEST MODE FOR CARRYING OUT THE INVENTION

The present invention is described below based on preferred embodiments. Note that the present invention is not limited to the following embodiments. The following embodiments illustrate an example in which the present invention is applied to a honeycomb structure (porous body) used for a diesel particulate filter. Note that the present invention is characterized in its detection position, and may also be readily applied to other porous bodies. In the drawings, identical elements and the like are indicated by identical symbols.

Figure 2:
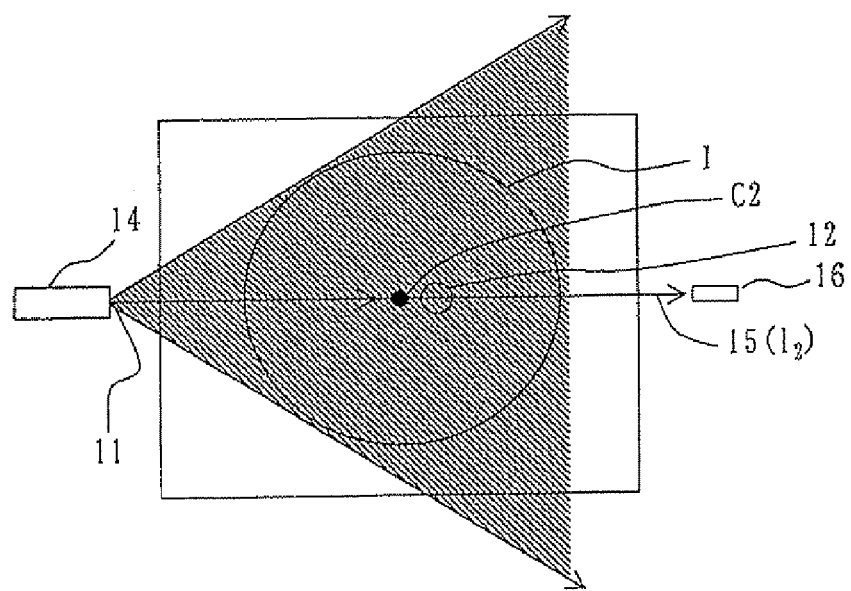
FIG. 2 is a schematic plan view of the detection device shown in FIG. 1.

FIG. 1 is a schematic side view showing an example of a detection device used for a detection method according to the present invention, and FIG. 2 is a plan view showing the detection device. As shown in FIGS. 1 and 2, the detection method according to the present invention includes applying a planar light beam 13 from a light source 14 to fine particles 12 discharged from a honeycomb structure 1 of porous body and detecting the light and shade of scattered light 15 caused by the fine particles 12 to specify the position of a defect, thereby detecting the defect.

Figure 7:
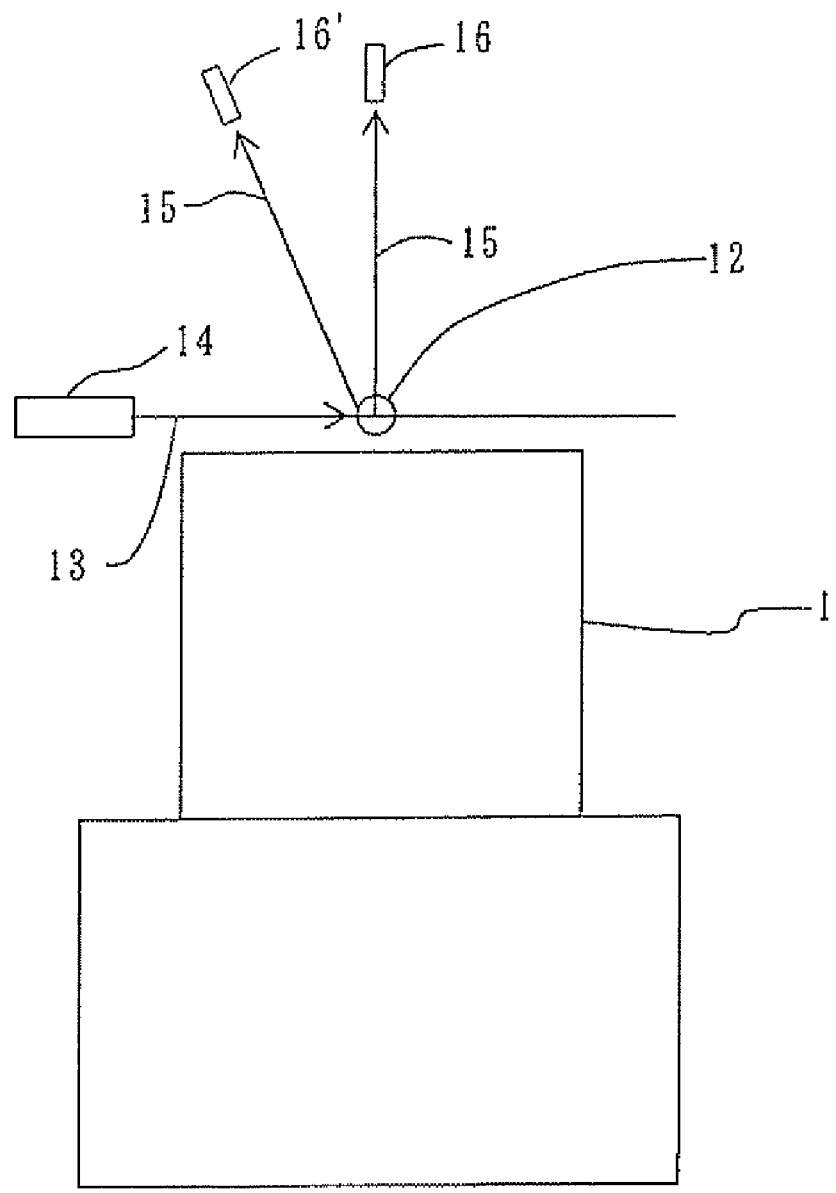
FIG. 7 is a side view schematically showing a detection device used for a related-art detection method.

As shown in FIG. 7, a related-art method detects the scattered light 15 at a detection position 16 perpendicular to the light beam or a detection position 16' closer to the light source 14 than the detection position 16. This aims to prevent the light beam 13 that travels straight from the light source 14 from directly coming in sight.

However, it was found that the light and shade of the scattered light can be detected with higher sensitivity at a position facing the light beam 13, as shown in FIGS. 1 and 2. The term "position facing the light beam 13" used herein refers to a position at which angles $\theta_1$ and $\theta_2$ defined below are less than 90°.

Figure 3:
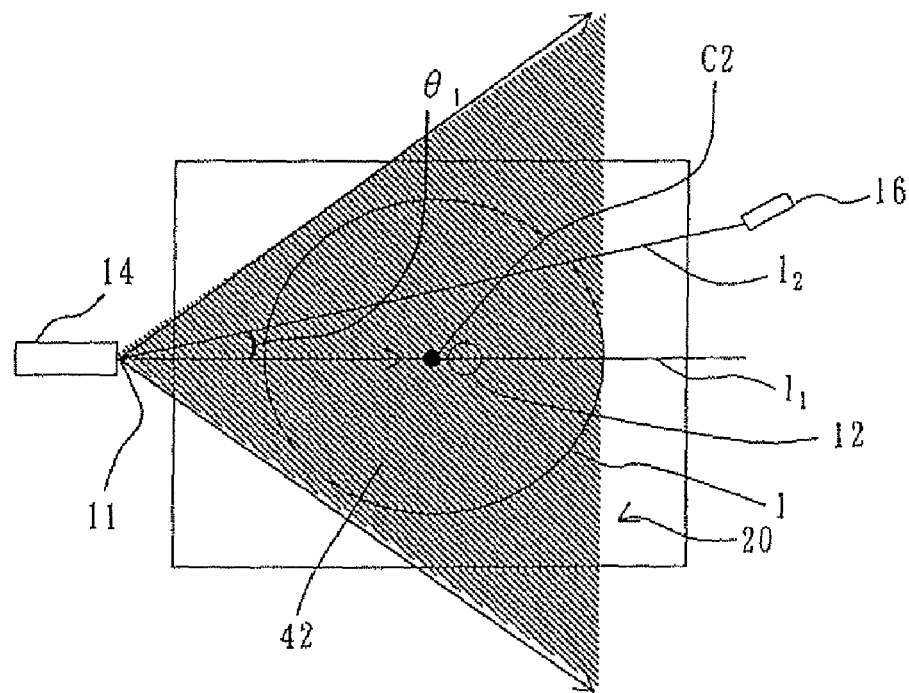
FIG. 3 is a schematic plan view showing another example of a detection device used for a detection method according to the present invention.

FIG. 3 is a schematic plan view showing another example of the detection device used in the present invention. FIG. 3 shows the positional relationship between the light source 14, the porous body 1, and the detection position 16 in a plane 20 formed by the light beam. As shown in FIG. 3, when the light source 14 that emits the light beam is defined as an origin 11, a position in the plane 20 formed by the light beam corresponding to a center C1 of an end face 42 of the porous body 1 through which the fine particles 12 are discharged is defined as a center point C2, a straight line that extends from the origin 11 toward the center point C2 is defined as $l_1$, a straight line that extends from the origin 11 toward the detection position 16 of the scattered light is defined as $l_2$, and the angle formed by the straight line $l_1$ and the straight line $l_2$ in the plane 20 formed by the light beam is defined as $\theta_1$, it is preferable to detect the light and shade of the scattered light at a detection position at which the angle $\theta_1$ is 0 to 80° from the viewpoint of improving the detection sensitivity. The term "position in the plane 20 formed by the light beam corresponding to the center C1 of the end face 42 of the porous body 1 through which the fine particles 12 are discharged" refers to an intersection point of the plane 20 formed by the light beam and a perpendicular line drawn from the center C1 to the plane 20. The term "center C1 of the end face 42" refers to a position corresponding to the center of gravity of the end face 42. For example, when the end face 42 is circular, the term "center C1 of the end face 42" refers to the center point of the circle. When the end face 42 is square, the term "center C1 of the end face 42" refers to the intersection point of the diagonal lines of the square. The origin 11 refers to a position (i.e., light source 14) at which the light beam is emitted. The angle $\theta_1$ is more preferably 45° or less, and particularly preferably 20° or less from the viewpoint of improving the detection sensitivity.

Figure 4:
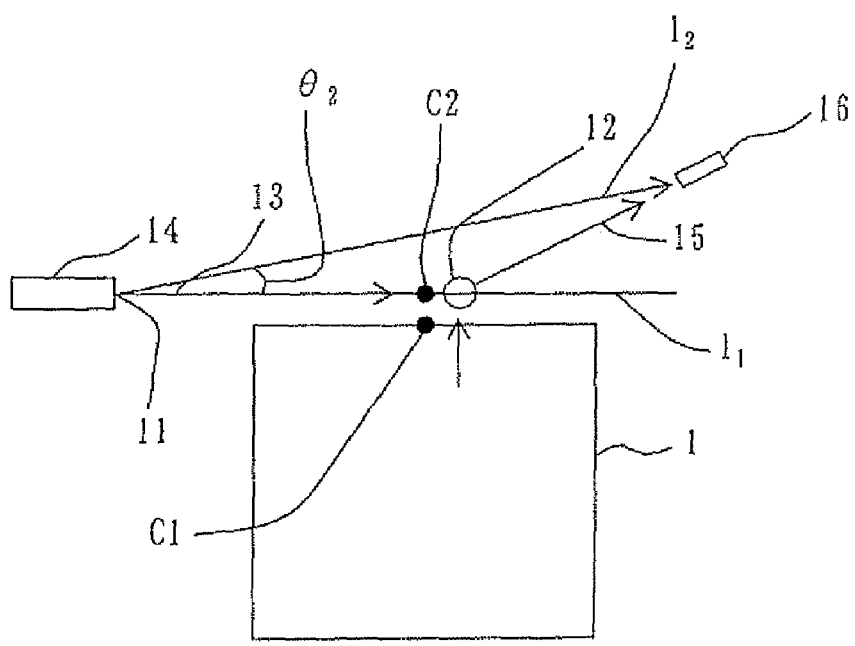
FIG. 4 is a schematic side view of the detection device shown in FIG. 3.

FIG. 4 is a side view of the light source 14, the porous body 1, and the detection position 16 shown in FIG. 3. The angle formed by the plane 20 formed by the light beam and the straight line $l_2$ is defined as $\theta_2$. It is preferable to detect the light and shade of the scattered light at a detection position at which the angle $\theta_2$ is 10 to 80° from the viewpoint of improving the detection sensitivity. The angle $\theta_2$ is more preferably 20 to 60°, and particularly preferably 20 to 45° from the viewpoint of improving the detection sensitivity.

The positional relationship between the light source 14 (origin 11) and the porous body 1 may be appropriately set corresponding to the size and the shape of a sample and the laser irradiation angle. It is preferable that the light source 14 and the porous body 1 be positioned so that the laser light can be efficiently applied over the entire end face 42.

The intensity of the scattered light is affected by the particle diameter of the fine particles 12 and the wavelength of the light beam 13. The intensity of the scattered light in the forward direction increases as the particle diameter (D) of the fine particles 13 increases and the wavelength ($\lambda$) of the light beam 13 decreases so that the detection sensitivity increases. Specifically, the light and shade of the scattered light can be detected with higher sensitivity by increasing the value (D/$\lambda$).

The particle diameter (D) is determined depending on the pore size of a normal (non-defective) portion of the sample. Specifically, it is necessary that the particle diameter (D) be a value that ensures that the fine particles 12 are discharged through the pores of a normal portion of the sample. The intensity of the scattered light in the forward direction can be increased by increasing the particle diameter (D) within such a range. Since the pore size of a defect portion is necessarily larger than the pore size of a normal portion, the fine particles are necessarily discharged through the defect portion. The particle diameter (D) is appropriately determined corresponding to the pore size of the sample. The average particle diameter of the fine particles is preferably 1 to 10 μm, and particularly preferably 5 to 10 μm. This range is preferably employed when inspecting a defect in a diesel particulate filter.

It is also preferable to reduce the wavelength ($\lambda$) in order to increase the intensity of the scattered light in the forward direction. It is preferable that the light beam be visible light. This enables the light and shade of the scattered light to be detected with the naked eye or using a camera or the like so that the cost of the detection device can be reduced. The wavelength ($\lambda$) is preferably 400 to 800 nm, and more preferably 500 to 700 nm. Laser light is normally used as a light beam having such a wavelength, Laser light may be emitted from a solid-state laser, a gas laser, a semiconductor laser, a dye laser, a free-electron laser, or the like.

When detecting a defect by observing the scattered light with the naked eye, it is necessary to use a light source compliant with Class 1 (maximum output: 390 nW) defined in JIS C 6802 from the viewpoint of safety. As shown in FIG. 5, it is preferable to dispose a shading plate 21 from the viewpoint of safety so that the light beam from the light source 14 does not directly come in sight.

A process of the defect detection method is described below taking an example of a defect detection method suitable for a honeycomb structure used for a diesel particulate filter.

As shown in FIG. 6, the honeycomb structure 1 used for a diesel particulate filter normally includes porous partition walls 2 that form a plurality of cells 3 which are formed through the honeycomb structure 1 in the axial direction, and plugging portions 4 that alternately plug the cells 3. Exhaust gas from a diesel engine is introduced into the cells 3 that is not plugged on one end face 44, enters the adjacent cells 3 through the porous partition walls 2, and is discharged through the other end face 42. The partition walls 2 function as a filter to trap particulate matter.

The honeycomb structure 1 is placed on a fine particle chamber 10, as shown in FIG. 1. The fine particles 12 are then produced in the fine particle chamber 10. The fine particles 12 may be produced by burning incense such as an incense stick, producing water fine particles utilizing dry ice, liquid nitrogen, an atomizer, or the like, or utilizing a commercially available ethylene glycol standard particle production device, for example.

The fine particles produced are introduced into the honeycomb structure 1 (i.e., inspection target). The fine particles may be introduced into the honeycomb structure 1 by an arbitrary method. For example, it is preferable to accumulate the fine particles in the fine particle chamber 10 until a specific concentration is reached, and then apply a specific pressure to the fine particle chamber 10 to introduce the fine particles into the honeycomb structure 1 through the one end face 44. The concentration of the fine particles 12 to be introduced is not particularly limited. The concentration of the fine particles 12 may be appropriately selected. The concentration of the fine particles 12 may be measured using a transmission laser sensor. The differential pressure between the side where the fine particles 12 are introduced and the side where the fine particles 12 are discharged is not particularly limited. A turbulent flow can be suppressed by reducing the differential pressure so that the detection sensitivity can be improved. On the other hand, if the differential pressure is too low, it takes too much time to detect a defect. The differential pressure is preferably 10 to 30 Pa. It is preferable to provide a pressure gage in the fine particle chamber 10 in order to control the differential pressure. In order to introduce the fine particles into the honeycomb structure 1 while maintaining a specific differential pressure air is normally supplied to the fine particle chamber 10. The flow rate of the air supplied is appropriately set corresponding to the size and the shape of the sample.

The fine particles 12 introduced into the honeycomb structure 1 pass through a defective partition wall to a large extent as compared with a non-defective partition wall. The fine particles 12 are then discharged through the other end face 42 (i.e., the end face where the fine particles are discharged) of the honeycomb structure 1. The light beam 13 is applied to the discharged fine particles 12, and scattered light caused by the fine particles 12 is detected over the entire end face 42 through which the fine particles are discharged to specify a position at which a large amount of scattered light is produced, thereby specifying the position of a defect. The scattered light may be detected by an arbitrary method. For example, it is preferable to detect the scattered light with the naked eye, or by photographing the scattered light using a camera such as a CCD camera. It is also preferable to record the scattered light as a video image or a still image using a camera.

When the porous body is a structure from which the fine particles are discharged through a specific end face (e.g., honeycomb structure), it is preferable to apply the light beam 13 so that the plane formed by the light beam 13 is parallel to the fine particle discharge end face, as shown in FIG. 1.

The sample is not particularly limited insofar as the sample is a porous body. The present invention may be suitably applied to detect a defect in a filter. Examples of the filter include a hollow fiber membrane) a bag filter, and the like in addition to the above-described diesel particulate filter. The present invention may be particularly suitably applied to a diesel particulate filter.

EXAMPLES

The present invention is further described below by way of examples. Note that the present invention is not limited to the following examples.

Sample
Honeycomb structure for diesel particulate filter
External shape: cylinder having a length of 254 mm and a diameter of 144 mm
Cell structure: cell density: 300 cells/in$^2$ (46.5 cells/cm$^2$), partition wall thickness: 300 μm
Porosity: 50%
Pore size: 20 μm

Example 1

The device shown in FIG. 5 was used. An incense stick was burnt in the fine particle chamber 10 to produce smoke having an average particle diameter of 5 μm. After the fine particle chamber 10 was filled with smoke, air was supplied to the fine particle chamber 10 at a pressure of 0.2 MPa and a flow rate of 8 l/min. Smoke produced from the incense stick was introduced into the sample at a differential pressure of 20 Pa. Planar laser light was applied from an NdYVO$_4$ laser (wavelength: 532 nm, output: 12 mW) to a position at a distance of 5 mm from the discharge end face of the sample. A shading plate was provided at a position facing the laser light. An observation window was provided at a position at which the angle $\theta_1$ was about 0 to 20° and the angle $\theta_2$ was about 20 to 30°. The light and shade of scattered light was visually observed through the observation window to detect the presence or absence of a defect in the sample and the position of a defect. The above inspection process was conducted on sixty-eight samples.

Comparative Example 1

The presence or absence of a defect and the position of a defect were inspected for the sixty-eight samples used in Example 1 in the same manner as in Example 1, except that the scattered light was observed at a position at which the angle $\theta_1$ was about 160 to 180° and the angle $\theta_2$ was about 20 to 30°.

When using the method according to Comparative Example 1, a defect was detected in nine samples among the sixty-eight samples. When using the method according to Example 1, a defect was detected in twelve samples. Table 1 shows the detection results for the samples for which a defect was detected in Example 1 and Comparative Example 1.

TABLE 1

| | Number of defects | |
|---|---|---|
| Sample No. | Comparative Example 1 | Example 1 |
| 1 | 1 | 1 |
| 2 | 1 | 2 |
| 3 | 1 | 1 |
| 4 | 1 | 1 |
| 5 | 1 | 1 |
| 6 | 2 | 2 |
| 7 | 1 | 1 |

TABLE 1-continued

| | Number of defects | |
|---|---|---|
| Sample No. | Comparative Example 1 | Example 1 |
| 8 | 0 | 1 |
| 9 | 1 | 1 |
| 10 | 0 | 1 |
| 11 | 0 | 1 |
| 12 | 1 | 1 |

Ten defects in total were detected by the method according to Comparative Example 1, while fourteen defects in total were detected by the method according to Example 1. The defects detected by the method according to Comparative Example 1 were also detected by the method according to Example 1. Therefore, it was confirmed that a defect could be detected with higher sensitivity by the method according to Example 1.

The intensity of the laser light was measured at the visual observation position employed in the method according to Example 1. The intensity thus measured was 50 to 62 nW. Specifically, it was confirmed that the method according to Example 1 was compliant with Class 1 (maximum output: 390 nW) defined in JIS C 6802 (i.e., naked eye observation is possible).

INDUSTRIAL APPLICABILITY

As described above, since the detection method according to the present invention detects a defect at a specific position, a defect can be detected with high detection sensitivity. Therefore, the detection method according to the present invention is useful for detecting a defect in a porous body (particularly a filter such as a diesel particulate filter).

The invention claimed is:

1. A method of detecting a defect in a porous body, the method comprising:
    applying a planar light beam to fine particles discharged from the porous body, and
    detecting the light and shade of scattered light caused by the fine particles to specify the position of a defect, the light and shade of the scattered light being detected at a position facing the light beam, wherein,
    a light source that emits the light beam is defined as an origin, a position in a plane formed by the light beam corresponding to a center of an end face of the porous body through which the fine particles are discharged is defined as a center point, a straight line that extends from the origin toward the center point is defined as $l_1$, a straight line that extends from the origin toward the detection position of the scattered light is defined as $l_2$, and the angle formed by the straight line $l_1$ and the straight line $l_2$ in the plane formed by the light beam is defined as $\theta_1$, and the light and shade of the scattered light is detected at a detection position at which the angle $\theta_1$ is 0 to 80° and,
    a straight line that extends from the center of the end face of the porous body to the detection position of the scattered light is defined as $l_3$, and the angle formed on the side of the porous body opposite the light source by the straight line $l_1$ and straight line $l_3$ is less than 90°.

2. The method according to claim 1, wherein, the angle formed by the plane formed by the light beam and the straight line $l_2$ is defined as $\theta_2$, and the light and shade of the scattered light is detected at a detection position at which the angle $\theta_2$ is 10 to 80°.

3. The method according to claim 1, wherein the distance between the origin and a fine particle discharge end face of the porous body is 1 to 10 mm.

4. The method according to claim 1, wherein the porous body is a filter.

5. The method according to claim 1, wherein the filter is a diesel particulate filter.

* * * * *